United States Patent
Ferguson

(10) Patent No.: US 10,258,411 B1
(45) Date of Patent: Apr. 16, 2019

(54) VIDEO PROCESSING HEADBAND

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

(*) Notice: Subject to any disclaimer, the term of this patent is extended or adjusted under 35 U.S.C. 154(b) by 665 days.

(21) Appl. No.: 14/510,364

(22) Filed: Oct. 9, 2014

Related U.S. Application Data

(60) Provisional application No. 61/981,695, filed on Apr. 18, 2014.

(51) Int. Cl.
| | |
|---|---|
| H04N 5/00 | (2011.01) |
| A61B 19/00 | (2006.01) |
| H04N 5/225 | (2006.01) |
| H04N 7/18 | (2006.01) |
| H04N 5/917 | (2006.01) |

(52) U.S. Cl.
CPC ...... *A61B 19/5212* (2013.01); *A61B 19/5202* (2013.01); *H04N 5/2256* (2013.01); *H04N 5/917* (2013.01); *H04N 7/183* (2013.01)

(58) Field of Classification Search
CPC ............ A61B 19/5212; A61B 19/5202; H04N 5/2254; H04N 5/2256
USPC .................................................. 348/77, 158
See application file for complete search history.

(56) References Cited

U.S. PATENT DOCUMENTS

| | | | |
|---|---|---|---|
| 4,616,257 A | 10/1986 | Kloots et al. | |
| 4,797,736 A * | 1/1989 | Kloots | F21V 21/084 |
| | | | 348/370 |
| 5,469,211 A | 11/1995 | Maruichi et al. | |
| D415,285 S | 10/1999 | Bishop | |
| 6,224,227 B1 * | 5/2001 | Klootz | F21V 33/0052 |
| | | | 348/370 |
| 6,714,141 B2 | 3/2004 | Kennedy | |
| 7,465,078 B2 | 12/2008 | Chang | |
| 7,512,006 B2 | 3/2009 | Yamazaki | |
| 8,262,560 B2 | 9/2012 | Whitman | |
| 2004/0141312 A1 | 7/2004 | Henning et al. | |
| 2004/0237969 A1 * | 12/2004 | Fuller | A61H 35/02 |
| | | | 128/858 |

(Continued)

FOREIGN PATENT DOCUMENTS

| | | | | |
|---|---|---|---|---|
| CA | 2773212 A1 * | 9/2013 | | A42B 3/10 |
| WO | 2009063224 A2 | 5/2009 | | |

*Primary Examiner* — Zhihan Zhou
(74) *Attorney, Agent, or Firm* — Timothy E. Siegel Patent Law, PLLC; Timothy E. Siegel

(57) ABSTRACT

A video headband assembly, having a headband structure, made at least in part of polymeric material, a battery port, a power management network having at least one output lead, and which supplies power from the battery port to the output lead and a multi-pin connector, accessible from outside the headband structure. Also, a video data signal transformation network is supported within the polymeric material of the headband structure and electrically connected to the multi-pin connector. Finally, a first video data signal input to the multi-pin connector is transformed by the video data signal transformation network, which produces a transformed video data signal in response to the first video data signal.

13 Claims, 9 Drawing Sheets

(56) References Cited

U.S. PATENT DOCUMENTS

| | | | | |
|---|---|---|---|---|
| 2005/0078095 A1* | 4/2005 | Ung | G06F 3/0421 | 345/175 |
| 2006/0171539 A1* | 8/2006 | Winningstad | H04M 1/05 | 380/270 |
| 2007/0237491 A1* | 10/2007 | Kraft | G02B 27/017 | 386/230 |
| 2008/0170838 A1* | 7/2008 | Teetzel | A42B 3/042 | 386/358 |
| 2009/0033736 A1* | 2/2009 | Thomason | H04N 7/147 | 348/14.02 |
| 2010/0328471 A1* | 12/2010 | Boland | G02B 13/004 | 348/207.99 |
| 2011/0077548 A1* | 3/2011 | Torch | A61B 3/112 | 600/558 |
| 2011/0145978 A1* | 6/2011 | Harbin | G02B 7/002 | 2/209.13 |
| 2012/0304767 A1* | 12/2012 | Howard | A42B 3/046 | 73/504.03 |
| 2013/0088582 A1* | 4/2013 | Moinzadeh | H04N 5/2251 | 348/77 |
| 2013/0121005 A1 | 5/2013 | Dahmen | | |
| 2014/0053318 A1* | 2/2014 | Fitzgerald | A42B 1/006 | 2/209.13 |
| 2014/0160250 A1* | 6/2014 | Pomerantz | H04N 5/23229 | 348/47 |
| 2014/0198484 A1* | 7/2014 | Feustel | F21L 4/00 | 362/105 |
| 2014/0267615 A1* | 9/2014 | Tapia | H04N 13/0203 | 348/46 |
| 2014/0296669 A1* | 10/2014 | Gertsch | A61B 5/6803 | 600/324 |
| 2015/0192286 A1* | 7/2015 | Hansen | F21V 29/002 | 362/235 |
| 2015/0195431 A1* | 7/2015 | Pacurariu | G03B 17/56 | 348/375 |
| 2016/0015289 A1* | 1/2016 | Simon | A61B 5/04842 | 600/301 |

* cited by examiner

VIDEO PROCESSING HEADBAND

RELATED APPLICATIONS

This application claims priority from provisional application Ser. No. 61/981,695 filed Apr. 18, 2014.

BACKGROUND

Medical headlamp assemblies having attached video cameras are old. These assemblies, however, tend to be heavy and are tethered by cables to a base station. This potentially interferes with the wearer's freedom of movement and may prove to be a distraction during delicate surgical procedures. For medical headlamp assemblies that must be physically tethered, in order to power the headlamp, little benefit could be gained by equipping the assembly with a wireless, as opposed to a wired, camera or vision system.

Untethered medical headlamp assemblies, having efficient lamps that permit the use of battery packs on the headband, are currently available. Typically, an adjustable linkage attaches the lamp to a headband. Although it might at first seem possible to simply attach an existing wireless video camera to the lamp, so that the camera images the area that is being illuminated, size, mass and power constraints make this an undesirable solution.

Installing a wireless video camera assembly directly on the lamp adds to the weight of the lamp/camera combination, and results in a requirement for a stiffer linkage, to prevent the lamp/camera from drooping. But a stiffer linkage is undesirable as this reduces the ease of adjustment. Also, a bulkier lamp/camera unit may act as a distraction to the wearer, who has some awareness of an element above the lamp, very near his forehead. Finally, a greater mass results in greater inertia when the wearer rotates his head, resulting in an unpleasant sensation during head rotation, and more torque at the location where the linkage holding up the lamp meets the headband.

Moreover, transmitting raw video over a WI-FI link can consume upwards of 2 watts of power. This means that a complete WI-FI camera system would consume more power than the medical headlamp, thereby requiring over-frequent battery swap-outs, and appearing impractical. The data compression necessary to reduce the required WI-FI data rate requires components that are bulky enough so that including them in the video camera housing, makes that housing bulky and heavy to the point of impracticability.

Another problem encountered, is that of addressing the differing requirements of different physicians, with different arm lengths, and practicing different types of surgery. A manually adjustable system requires a free hand, something that is typically not available in surgery. Also, such a system can go out of adjustment, especially if accidentally touched by an assistant. Yet a fixed system will be out of focus for those doctors who prefer to keep the head at a different distance from other doctors, perhaps due to having a shorter or longer arm length.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a video headband assembly, having a headband structure, made at least in part of polymeric material, a battery port, a power management network having at least one output lead, and which supplies power from the battery port to the output lead and a multi-pin connector, accessible from outside the headband structure. Also, a video data signal transformation network is supported within the polymeric material of the headband structure and electrically connected to the multi-pin connector. Finally, a first video data signal input to the multi-pin connector is transformed by the video data signal transformation network, which produces a transformed video data signal in response to the first video data signal.

In a second separate aspect, the present invention may take the form of a method of forming a wireless transmission of video of a medical procedure, which uses a medical headlamp assembly that includes a headband structure, a medical headlamp, operatively mounted on the headband structure, and a video camera, operatively mounted on the headband. Also, a data processing and wireless transmitter assembly is included in the assembly and is communicatively connected to the video camera. In the method, the medical headlamp is used to illuminate the medical procedure and the video camera is used to produce a video signal, which is received by the data processing and wireless transmitter assembly, which transmits a signal representative of the video signal.

In a third separate aspect, the present invention may take the form of a headband video recording system, that can be personalized for a user having preferences, and that includes a headband, an articulated linkage, supported on the headband, and an image sensor unit, supported by the articulated linkage. Also, a lens stack unit is positioned in front of and is supported by the image sensor unit. Finally, the lens stack unit may be adjusted to a specific focal length and field of view, and set to maintain the specific focal length and field of view, thereby meeting the preferences.

In a fourth separate aspect, the present invention may take the form of a medical headlamp and camera system having an articulated linkage-and-headlamp assembly, including an articulated linkage supporting a headlamp and a video camera supported by the articulated linkage-and-headlamp assembly, and which produces a first video data signal. Also, a headband assembly, supports the articulated linkage-and-headlamp assembly, and includes at least one battery port, which supports a battery, and further including an electrical network, including a microcontroller, that supplies electrical power to the headlamp and the video camera from the battery, in reliance on computations performed by the microcontroller. Finally, a data compression network, electrically connects to the video camera, and receives the first video data signal and compresses it into a compressed data signal and a wireless transmitter, is supported by the headband assembly and electrically connected to the data compression network to wirelessly transmit the compressed data signal.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Definitions: A data signal is any signal that represents a stream of data. Transforming a data signal means changing the representation of a data value, for example changing from a signal in which a "1" is represented by 0.34 volts on a data line, to a signal in which a "1" is represented by 2.3 volts or a signal where a "1" is represented by a value of an electromagnetic signal, present in the air. Transforming a data signal also includes transforming the data represented by the data signal by, for example, compressing it or encrypting it.

Figure 1:
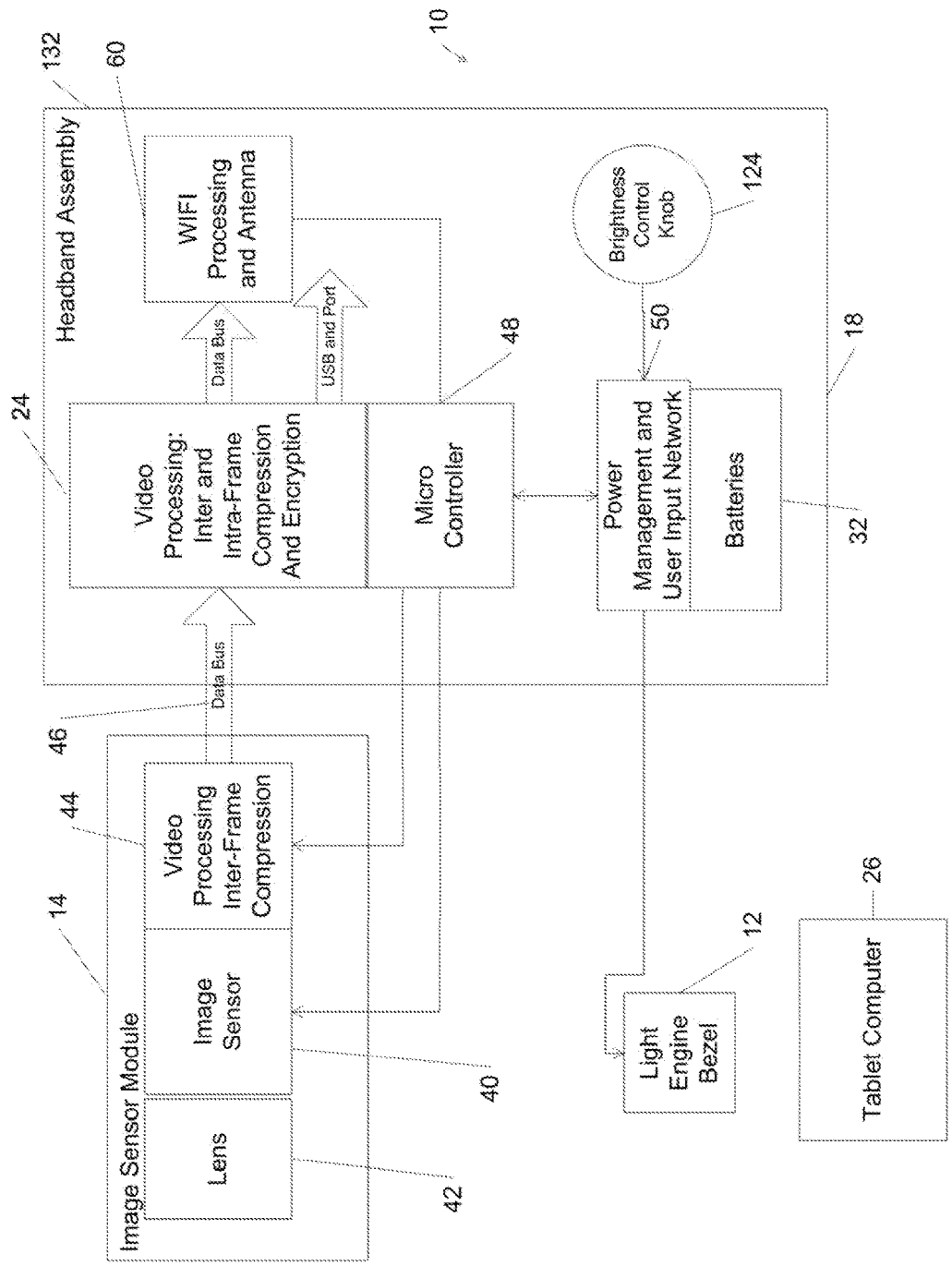
FIG. 1 is a block diagram of the electrical power and logic of a medical headlamp and video camera headband assembly according to a preferred embodiment of the present invention.
Figure 2:
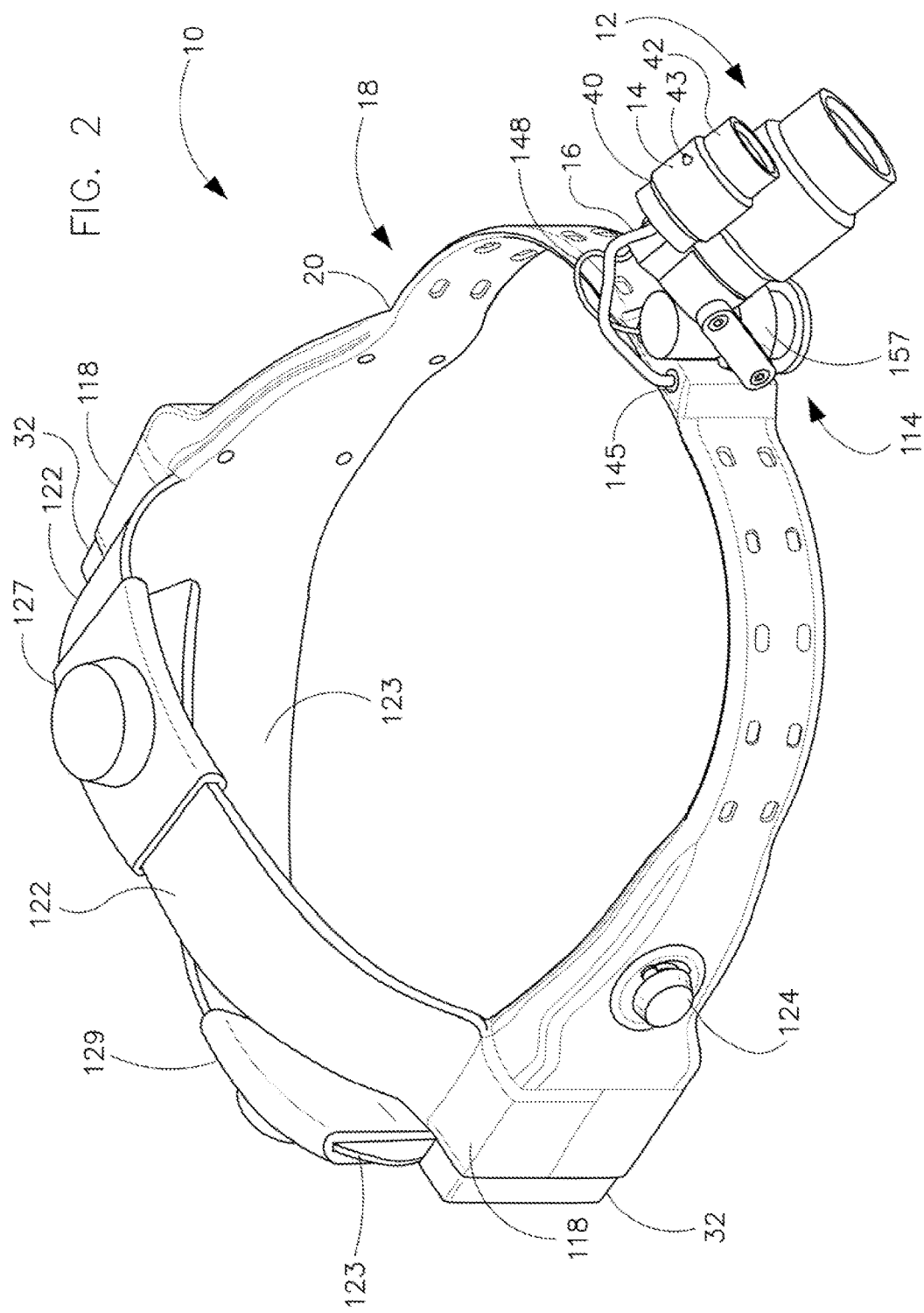
FIG. 2 is an isometric side-top view of a medical headlamp assembly according to the present invention, configured to be received onto a user's head.

Referring to FIGS. 1 and 2, a preferred embodiment of a medical headlamp and camera system 10 includes a headlamp (also referred to as "light engine bezel") 12 and an image sensor module (also referred to as "video camera" or simply "camera") 14. Image data gathered by module 14 is sent over a multi-conductor cable 16 to a headband assembly 18 that includes a headband structure 20 and internal electrical conductors that lead to a principal video processor 24, which processes and wirelessly transmits the image data. A tablet computer 26 communicates with system 10, by way of Wi-Fi Processing and Antenna 60, and is configured to receive the wireless image data, and to display and record it as commanded by a user. Tablet computer 26 is also configured to wirelessly command module 24, through Wi-Fi unit 60, which is connected to micro-controller 48, to for example, command it to command the image sensor module 14 to begin recording. In one preferred embodiment, tablet computer 60 may use the same communications route to adjust the brightness of headlamp 12. A pair of battery ports 118, support batteries 32 that power the system, with wire 148 supplying headlamp 12 with electrical power. In one preferred embodiment tablet computer 26 includes a microphone and voice command recognition technology, so that it can be used to relay voice commands to assembly 10.

Image sensor module 14, includes an image sensor 40, a lens stack 42 and a front end video processor 44. Lens stack 42 sets the field of view and focus distance of module 14. In one preferred embodiment, lens stack 42 is adjustable to set a precise focus length based on the anticipated distance at which the camera will be viewing a medical procedure, and can be set in place, after adjustment by, for example, set screw 43. In a variant of this, differing versions of a front end of the lens stack 42 will be made available, each optimized for a different anticipated viewing distance, so that the user may select the front end that best suits his needs. A surgeon may set the focal length of the lens stack 42 of his assembly 10 based on his arm length.

Image sensor 40 and video processor 44 may collectively take the form of the Aptina AS0260, which includes a system-on-a-chip and has the capability to perform intra-frame data compression, more specifically in accordance with the JPEG (Joint Photographic Experts Group) standard or MJPEG standard. In an alternative embodiment image sensor 40 may take the form of a sensor with an ultra-low energy change sensing mode, so that the camera can draw as little power as possible for an image that is not undergoing significant change, but can be commanded to take much higher resolution and higher frame rate imagery as soon as an image change is detected.

A multi-line data bus 46, of which multi-connector cable 16 (FIG. 2) forms a part, connects the image sensor module 14 to a principal video processor 24. A control unit 48 controls the system 10. The principal video processor 24 and the control unit 48, collectively may take the form of an Ambarella A7LW system on a chip (SoC). This unit includes an ARM processor, which serves as control unit 48 and a video processing unit, which serves as principal video processing unit 24, which compresses and encrypts the data, according to an interframe scheme of compression. In one preferred embodiment, the H.264/MPEG-4 AVC standard is used for the data compression and encryption.

Also within headband assembly 18, a power management network 50, receives power from a battery set 32 and delivers power to the light engine bezel 12, the image sensor module 14 and the power consuming units of the headband assembly 18. A brightness control knob 124 permits a user to adjust the brightness of the bezel 12. In one preferred embodiment, knob 124 also acts as an on/off switch for system 10, so that as knob 124 is rotated to an extreme position in a first direction, a "click" sound is made and the entire system 10 is turned off. When rotated in the opposite direction a similar click sound is made and the system is turned on, with the WIFI unit 60 placed in listen mode, to receive a command from tablet computer 26, for image sensor 40 to begin recording, and bezel 12 to illuminate.

A WI-FI unit 60, including an antenna, broadcasts the data received from processing unit 24. System 10 also includes a USB port, for connection of a dongle or a USB cable.

The object of the data processing scheme implemented in both front end processor 44 and principal processor 24 is to determine and send the most important data that can be fit into the limited bandwidth available (about 100 MBPS or less) that can be used without using so much energy as to become burdensome to the operating room crew, which must swap out batteries that have been depleted. One technique that is used is the detection of the region of the frames that is illuminated by the bezel 12, and delivering only information representative of this region to WI-FI unit to be transmitted. A first order detection scheme tests for a border between bright and dim pixels, or otherwise detects the area illuminated by the bezel 12, and eliminates the pixels on the outside of this area. Further the data compression scheme is optimized for the type of data likely to be encountered during a surgery. In one preferred embodiment the data compression scheme is matched to an expected rate of change of imagery during surgery.

In another scheme, the rate of wireless transmission is slowed during periods when there is less movement in the field of view. In one embodiment a gravity sensor (plumb bob) is used to detect instances in which the surgeon is no longer viewing the surgical theater, so that the bezel 12 and camera 14 may be turned off. In one embodiment, these power saving devices can be left unused at the user's input to the contrary. In one embodiment an especially low transmit power wireless system is used, to reduce power consumption, take advantage of the nearness of the wireless receiver and avoid interference with other RF equipment in the medical environment. In one embodiment a blue-tooth system is used for transmitting the video signal. In one embodiment a maximum of two watt-hours of energy are used to power the bezel 12, the image sensor 14, the data compressor 24 and the wireless transmitter 60.

In one preferred embodiment a user selectable mode is provided in which the control unit adjusts the current delivered to bezel 12, in response to the brightness of the pixels within the illuminated area, thereby saving electricity when the illuminated circle is brighter than necessary. The user may opt out of this mode, to avoid possible complications.

Figure 3:
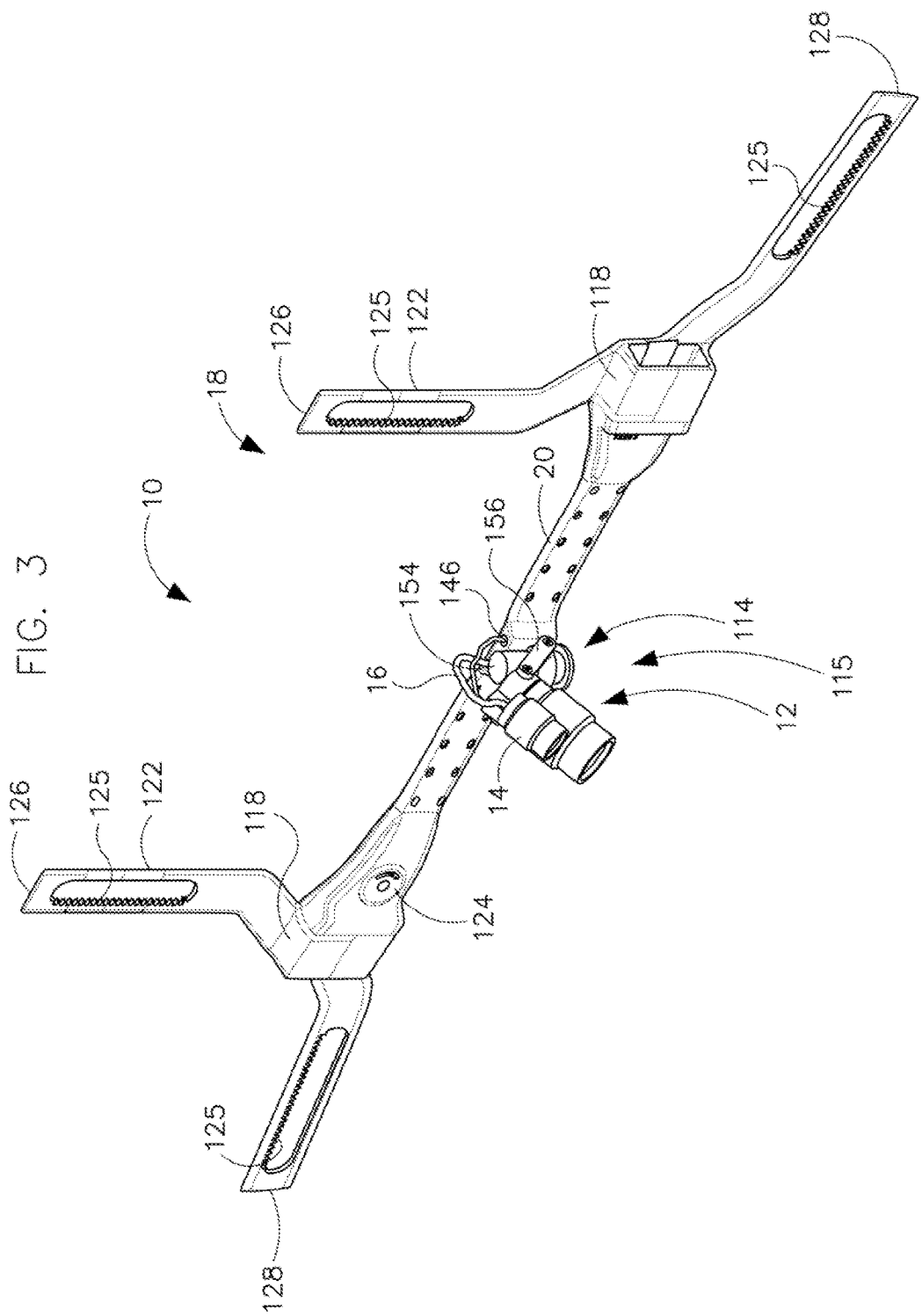
FIG. 3 is an isometric side-top view of the assembly of FIG. 2, but without the tightness adjustment elements, and with elements extended outwardly, in a plane.
Figure 5:
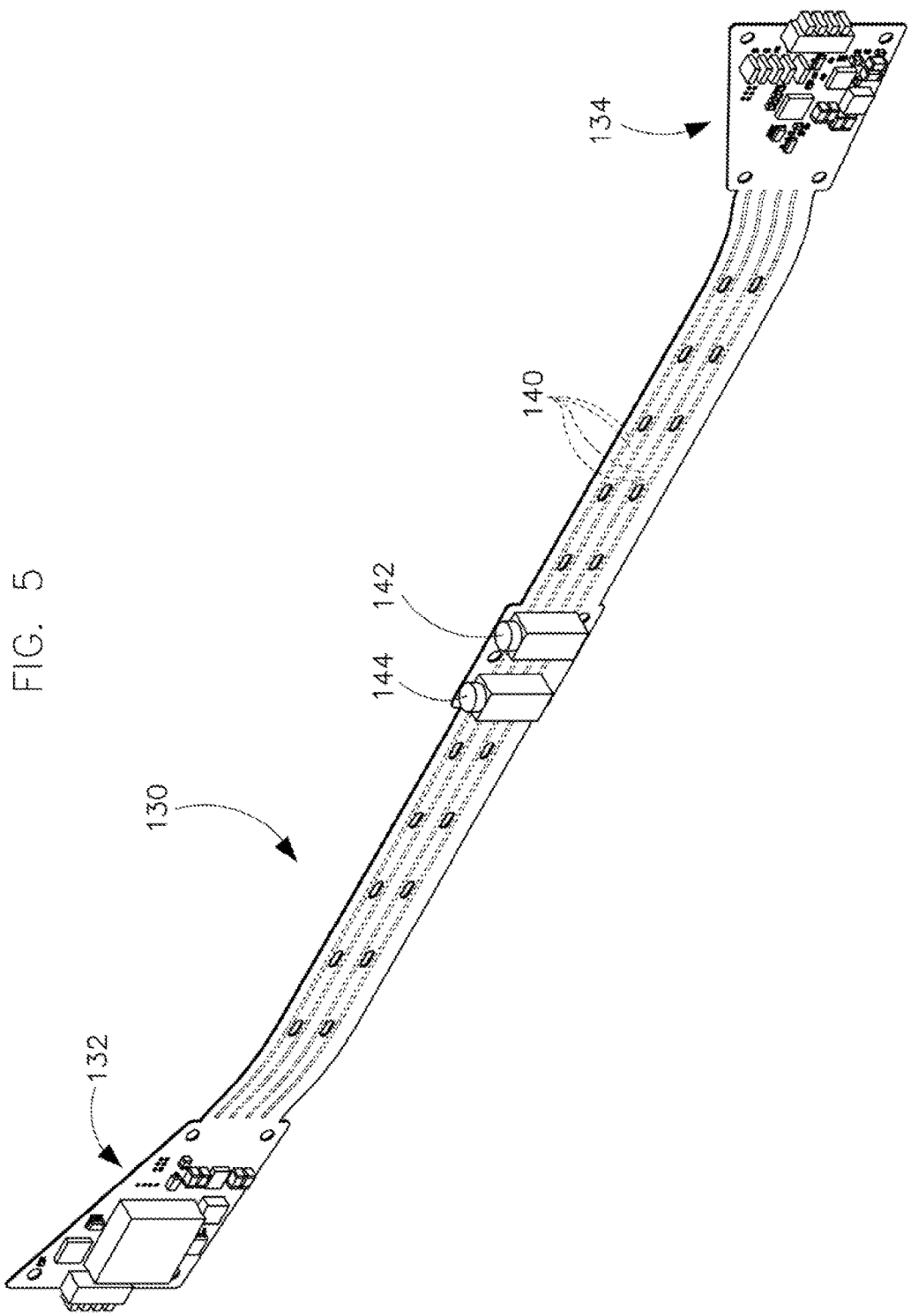
FIG. 5 is an isometric side-top view of a rigid-flex circuit element of the assembly of FIG. 3.
Figure 6:
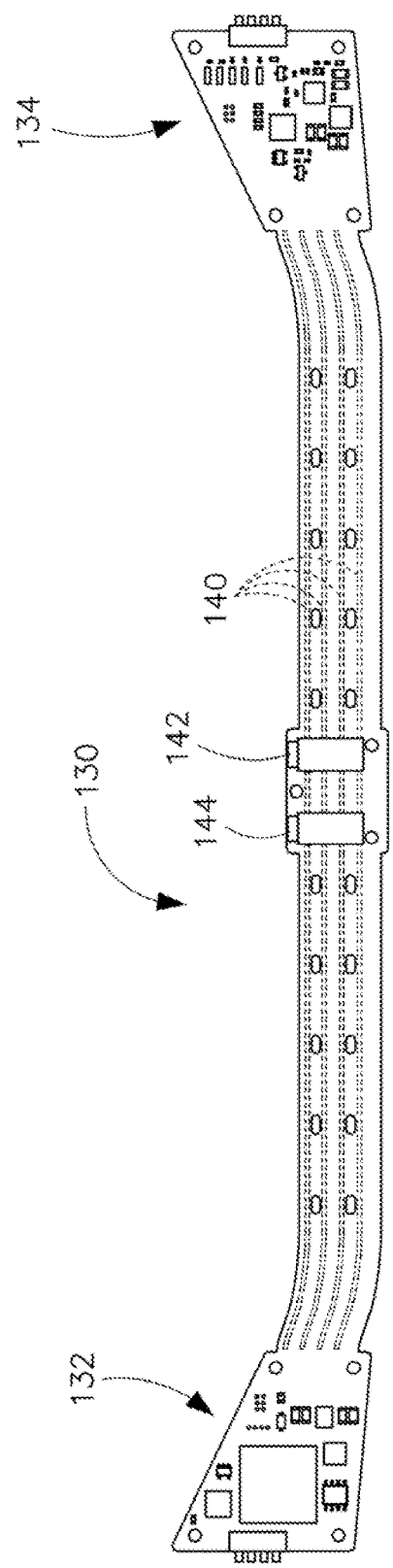
FIG. 6 is a front view of the rigid-flex circuit element of FIG. 5.
Figure 7:
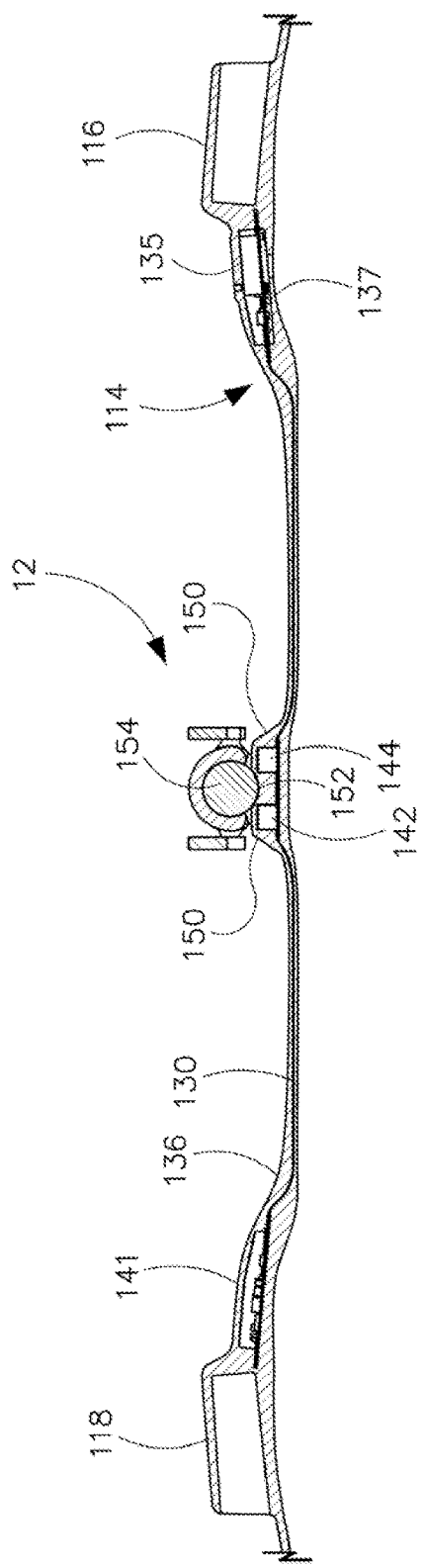
FIG. 7 is a section view of the assembly of FIG. 4, taken along view line 7-7 of FIG. 4.
Figure 8:
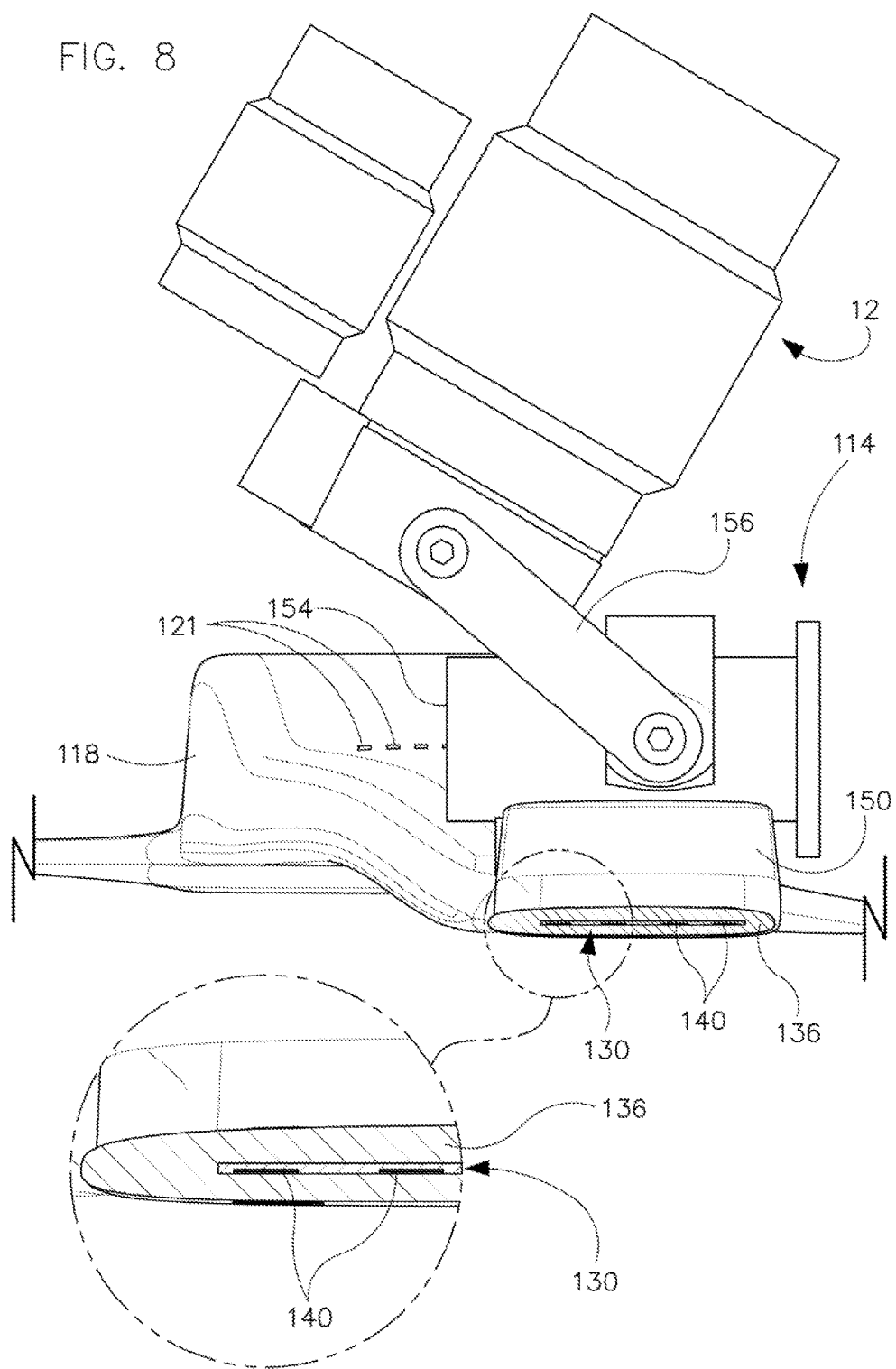
FIG. 8 is a section view of the assembly of FIG. 4, taken along view line 8-8 of FIG. 4.

Referring to FIGS. 2 and 3, in physical form, a preferred embodiment of the present invention is a medical headlamp assembly 10, having a light engine bezel 12, a video camera 14, an adjustable bezel support linkage 114, a headband assembly 18, defining a pair of battery sockets 118, bearing batteries 32, each in contact to a rigid-flex circuit insert 130 (FIG. 5). The linkage 114 and light engine bezel 12, collectively constitute an integrated articulated linkage-headlamp and camera assembly 115.

Figure 4:
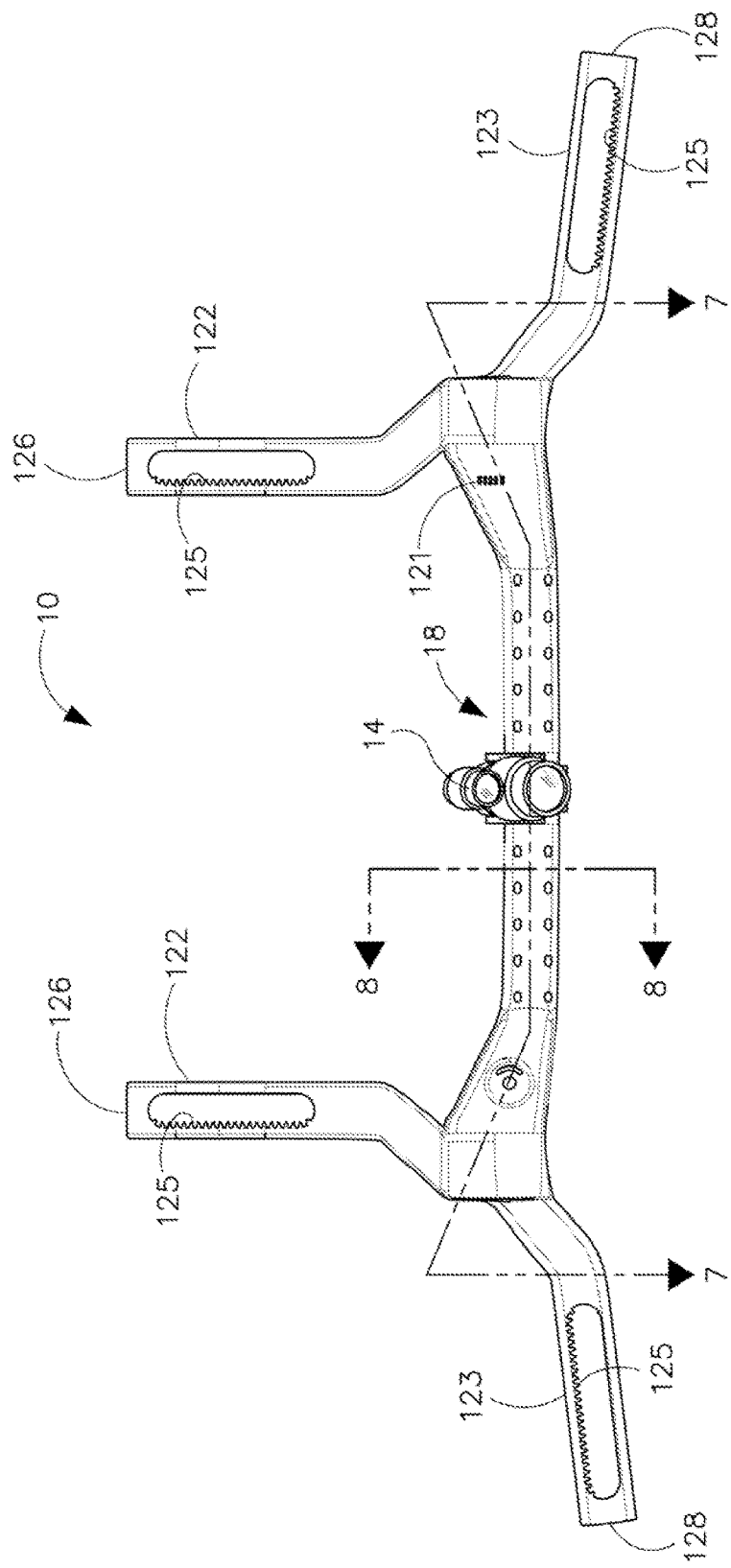
FIG. 4 is a front view of the assembly of FIG. 3.

The charge remaining in batteries 32 is indicated by a set of battery charge indicator lights 121 (FIG. 4). A head-top strap 122 and a head-back strap 123 form a part of headband assembly 18. As shown in FIG. 3 straps 122 and 123 are both formed from a pair of arms (126, 128) each having a serrated elongated opening 125. The two arms of the head-top band are drawn together by tightness adjust 127 which engages the serrations to adjust the length of the coupled arms, and the two arms of the head-back strap 123 are drawn together by tightness adjust 129. A brightness control knob 124 is also supported by headband assembly 18.

Referring now to FIG. 4-8 a rigid-flex circuit 130 is embedded into the center portion of headband assembly 18. Rigid-flex circuit is an industry term that describes a structure having both rigid and flexible portions, constructed by laminating together rigid and flexible layers and then removing the rigid layers in areas where flexibility is desired. In this application, the term "flex circuit" encompasses rigid-flex circuit, so that rigid-flex circuit is a type of flex circuit. Rigid-flex circuit 130 includes right and left-side rigid portions that support a right hand electrical network 132, and a left hand electrical network 134, respectfully. The electrical components of network 132 and 134 are connected together by a first set of conductive traces (not shown) that are internal to rigid-flex circuit 130. These traces are configured in a pattern designed to effect a predetermined scheme of connection. Rigid-flex circuit includes an additional rigid portion, right at the location where the linkage 114 connects to headband assembly 18.

The right hand network 132 is kept in an air pocket, protected by a right hand top can 135 (FIG. 7) and a right hand bottom can 137 (FIG. 7), both made of stainless steel that is 0.15 mm thick. The top can 135 is 4.5 mm high, whereas can 137 is 1.5 mm high. During the molding process, these cans 135 and 137 prevent the polymer material from contacting the components of network 132. Although bottom can 137 does create an area of some rigidity to the outside of strap assembly 18, it is covered by a 0.3 mm thick covering of relatively soft polymeric material 136, which greatly ameliorates this condition. A round indent (not shown) in can 137, which defines a hole (not shown) at its center, provides a seat for the head of a shaft (not shown) for the brightness control knob 124. On the left hand side, only a top can 141 (FIG. 7), having similar dimensions to and made of the same material as the top right hand top can 135, is required, due to a smaller component set, confined to the top of rigid-flex circuit 130. In an alternative preferred embodiment (not shown) a type of polymer that permits heat flow is used, thereby eliminating the need for cans 135, 137 and 141. In a preferred embodiment (FIG. 1), video processor 24 and microcontroller 46 are placed on the right side, as part of network 132, in can 135 to more directly receive input from the brightness control knob. In an alternative preferred embodiment, these elements are placed on the left side, as part of network 134, in can 141. In alternative preferred embodiments, one or more of the cans are larger than described here or are made of a material other than stainless steel, such as titanium.

Electrical networks 132 and 134 are electrically connected together, to bezel 12 and to video camera 14, by a second set of conductive traces 140, each of which extends either across the center of rigid-flex circuit 130 or from one of the electrical networks 132 and 134 to either a first jack 142 or a second jack 144. In a preferred embodiment first jack 142 accepts a plug 146 (FIG. 3) that through wire 148, supplies bezel 12 with electric power. When not in use for this purpose, jack 142 accepts a plug (not shown) from a voltage source, for recharging batteries 32. Second jack 144 accepts a plug 145 (FIG. 2) for the multi-conductor cable 16, that forms a portion of data bus 46 from video camera 14 to processing network 132 or 134. Although plug 145 is shown in the form of an audio plug, which may have several contacts, multi-pin forms are used in alternative preferred embodiments. Plug 146 and the wire attached to it may be considered an electrically conductive system of linkage 114, whereas first jack 142 may be considered a further electrically conductive element of headband assembly 18. Bezel 12 could be electrically connected to headband assembly 18 by a simple wire, in which case the portion of the wire in the linkage could still be considered an electrically conductive system and the portion in the headband could be considered a further electrically conductive element. Video camera 14 must be connected by a set of conductors because of the volume of data required to be moved.

In an alternative preferred embodiment, rigid-flex circuit 130 is replaced by a longitudinal flex circuit or a longitudinal rigid-flex circuit having a circuit board electrically and physically connected to either end, a right hand circuit board supporting and electrically connecting network 132 and a left hand circuit board supporting and electrically connecting network 134. In alternative preferred embodiments the pair of circuit boards is connected by a cable harness or a ribbon cable.

In a preferred embodiment, rigid-flex circuit 130 (together with jacks 142 and 144 and networks 132 and 134) is encased in a sheathing of polymer material 136 that also forms the top arms 126 and side arms 128. To produce the headband assembly 18, rigid-flex circuit 130 is suspended in a mold by shafts that extend through apertures for battery charge indicator lights 121. Polymer material in liquid phase is forced into the mold and after it has been allowed to cure, the shafts are withdrawn and the headband assembly 18 is ejected.

In a preferred embodiment sheathing polymer material 136 may be Styrene-Ethylene/Butylene-Styrene Block Copolymer or similar material, preferably having a shore durometer rating of between 50 and 60 in its cured state. In one preferred embodiment, the shore durometer rating is 55. The 100% modulus is preferably between 1800 and 2500 psi. The mold injection temperature is between 180° C. and 240° C. These materials are available from United Soft Plastics of Lawrenceville, Ga. In one preferred embodiment, an antimicrobial agent is added to the polymer material 136, to prevent fungal and bacterial growth on the surfaces of the material 136, in use. In a preferred embodiment MCX 122656 Antimicrobial Masterbatch, available from RTP Co., of Winona, Minn., which maintains a website at www.rtp-company.com, is added to the polymeric substance, in liquid state.

In prior art of battery bearing headbands, the battery sockets have been separated from the material contacting the user's head by a space for circuitry, whereas in the preferred embodiment, the circuitry has been placed in front of the battery, as opposed to a position interposed between the battery and the head. Also, the battery sockets 118 have been moved farther back on the head, relative to prior art headbands, so that the closest portion of the batteries 32 to the linkage is 153 mm from the linkage as measured along the headband as it curves about the head, or stated in a slightly different but equivalent manner, measured as it would be if the headband assembly were laid out flat. For most wearers, this places the forwardmost part of the batteries at a position just above the ears, so that a portion of batteries may extend in backward direction at the place where the head curves inwardly toward the back, thereby avoiding contact between the batteries and the head, and providing a greater balance in weight, yielding greater comfort.

There are a number of advantages to the resulting headband. First, as it is constructed as a unitary piece, there are no seams that in other systems provide a foothold for the growth of fungus, and seepage of users' cleaning fluid into interior cavities, which can potentially damage electrical networks 132 and 134. Also, in one prior art system the two pieces that were joined to form the band for the back of the head also formed the panels separating the batteries from the head. This piece was made of a harder polymer material than other portions of the headband, in part to resist the tendency of the batteries, which extended further from the head because of the interposed electrical network, to torque with the top being pulled by gravity downwardly, which could easily translate to away from the head. The use of a harder polymer, however, can result in discomfort over the hours required to complete some surgeries. In headband 18, the use over the entire assembly of polymer material 136 which in a preferred embodiment has a shore durometer reading of 55 is more comfortable, even over long periods of time. In addition, the traces 140 that link networks 132 and 134 permit communication that permits these networks to cooperate. In one preferred embodiment, the battery delivering power to the bezel 12 shifts periodically, for example as the voltage of the active battery passes below a threshold, the load of the optical assembly is shifted to the other battery 32, so that the batteries drain at the same rate, over time. Also, those traces leading from networks 132 and 134 to the jacks 142 and 144 for supplying bezel 12, and to the data port of camera 14, make external wires unnecessary. Such wires can present a snagging hazard.

A pair of parallel front-center vertical ridges 150 (FIGS. 7 and 8) are created by the encasement of jacks 142 and 144. The valley 152 between these ridges form an elongated seat for post 154, which is part of support linkage 114. When arms 156 (also part of linkage 114) are rotated, post 154 is torqued and in turn torques headband assembly 18. The structure of post 154 and ridges 150, however, help to diffuse this torque and material 136 helps to cushion the forehead from the torque, so that the operation of rotating arms 156 is not as uncomfortable to the wearer of headlamp and video camera system 10 as it would otherwise be. Linkage 114 includes a partial collar 157, which fits onto post 154. Moreover, partial collar 157 is removable from post 154, so that integrated unit 115, including headlamp 12 and camera 14, may be quickly removed from headband assembly 18, with plugs 145 and 146 pulled from jacks 142 and 144. Accordingly, if an electrical or mechanical problem is detected with either headlamp 12 or camera 14 the entire unit 115 may be quickly replaced with a spare. Alternatively, a first version of unit 115 can be quickly swapped out for a second version of unit 115, having specialized or more advanced properties.

Figure 9:
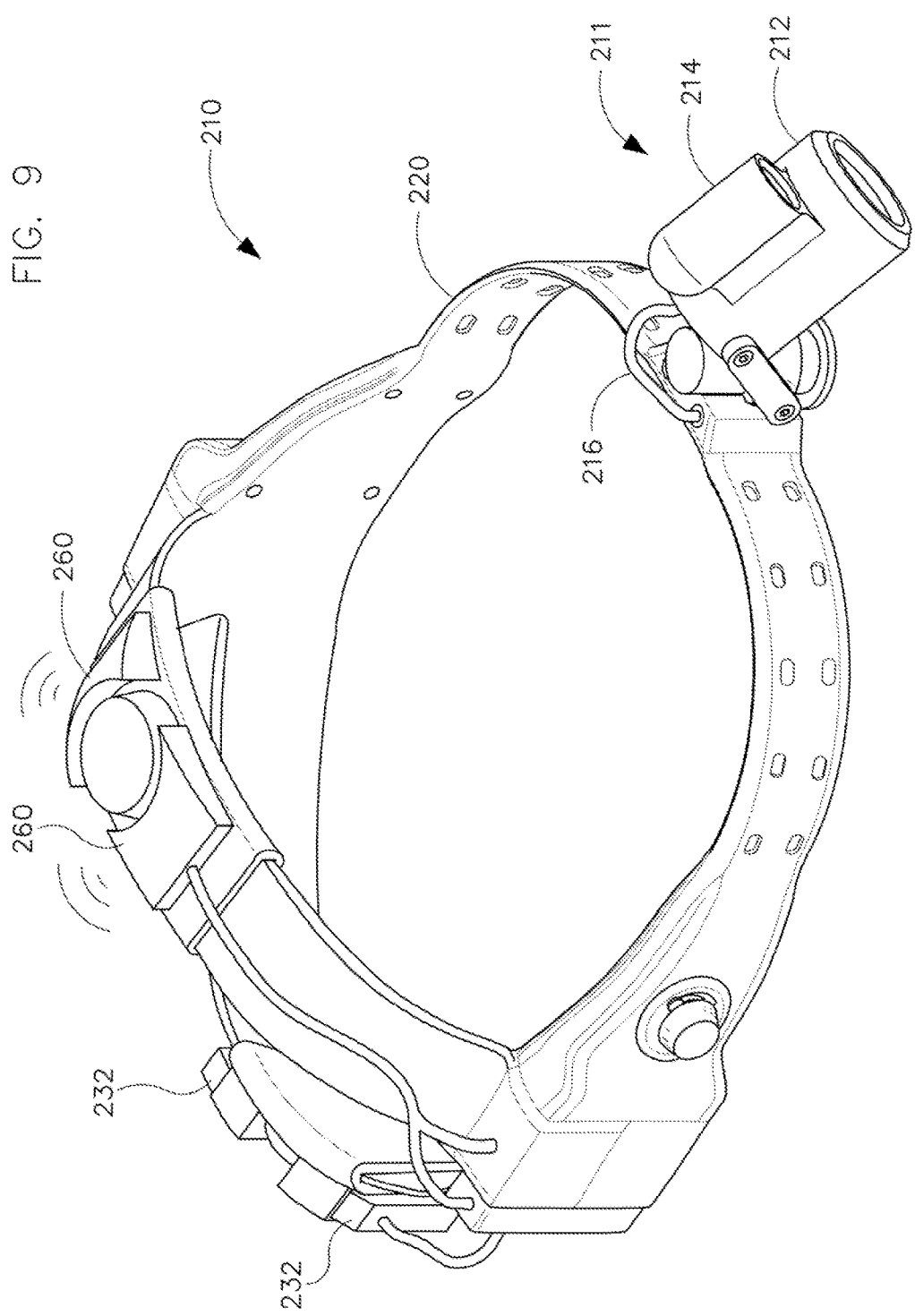
FIG. 9 is an isometric side-top view of a medical headlamp assembly, representing an alternative embodiment of the present invention, configured to be received onto a user's head.

Referring to FIG. 9, an alternative preferred embodiment of a medical headlamp assembly 210 includes a headlamp and camera unit 211, which includes a headlamp 212 and an image sensor module 214 joined together. A single cable 216 carries both electric power to unit 211, where it is divided interior to the housing between headlamp 212 and image sensor 214, and also carries data to and from sensor 214. A pair of antenna 260, driven by wire, are located on top of assembly 210 to have a greater chance of having an unblocked line-of-sight to a receiver, such as tablet computer 26. An additional pair of batteries are held at the back, in much the same manner as batteries 32. Assemblies 10 and 210 may be otherwise the same. In the embodiment of FIG. 9, special design features draw heat from the headlamp 12, away from the camera 14, to avoid overheating camera 14.

The ability to wirelessly broadcast the video signal of a surgery greatly eases the task of the teaching surgeon, who wishes to bring the student into the operating theater with him, without being tethered by a wire to receiving device or having an additional person actual in the operating room, with him. The greatly facilitated capability of creating a video display of the surgical procedure can be expected to enhance medical education, with the attendant result of better trained junior surgeons, performing their operations in a more expert manner.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A video headband assembly, comprising:
    (a) a headband structure, made at least in part of polymeric material, and defining at least one inner cavity encased in polymeric material;
    (b) a battery port;
    (c) a power management network having at least one power output connector, and which supplies power from said battery port to said power output connector, filling part of said at least one inner cavity;
    (d) a multi-contact data connector, accessible from outside said headband structure; and (e) a video data signal transformation network also filling part of said at least one inner cavity and electrically connected to said multi-contact connector, and wherein a first video data signal input to said multi-contact connector is transformed by said video data signal transformation network, which produces a transformed video data signal in response to said first video data signal, wherein said polymeric material of said headband structure has an exterior that is seamless, to deny fungal spores an anchor.

2. A medical headlamp and camera system, comprising:
(a) an articulated linkage-and-headlamp assembly, including an articulated linkage supporting a headlamp;
(b) a video camera supported by said articulated linkage-and-headlamp assembly, such that an adjustment to the pointing angle of said headlamp results in an equal adjustment to the pointing angle of said video camera, and which produces a first video data signal;
(c) a headband assembly, supporting said articulated linkage-and-headlamp assembly, and including at least one battery port, supporting a battery, and further including an electrical network, including a microcontroller, that supplies electrical power to said headlamp and said video camera from said battery, in reliance on computations performed by the microcontroller;
(d) a data compression network, electrically connected to said video camera, which receives said first video data signal and compresses it into a compressed data signal; and
(e) a wireless transceiver, supported by said headband assembly and electrically connected to said data compression network to wirelessly transmit said compressed data signal.

3. The system of claim 2, wherein said integrated circuit controls said headlamp responsive in part to said data representative of said first video data signal.

4. The system of claim 2, wherein said integrated circuit processes data representative of said first data signal by detecting a region illuminated by said headlamp and eliminating from further processing pixels outside of said illuminated region.

5. The system of claim 2, wherein said data compression network is controlled by said microcontroller.

6. The system of claim 2, wherein said integrated circuit decreases power to said headlamp, when data representative of said first video signal indicates that said headlamp is producing too much light.

7. The system of claim 2, wherein said system includes a single switch, which activates said headlamp, and places said wireless transceiver into a listen state, to receive a signal.

8. The system of claim 7, wherein said single switch is a knob, wherein one position of rotation, switches said system into an "off" state.

9. The headband assembly of claim 1, further wherein said video data signal transformation network includes a wireless transmitter, and wherein said transformed video data signal is a wireless signal.

10. The headband assembly of claim 1, further including an output data port connector, electrically connected to said video data signal transformation network and making said transformed video data signal to any matching connector.

11. The headband assembly of claim 1, wherein said multi-contact connector is a multi-pin connector.

12. The headband assembly of claim 1, wherein said multi-contact connector is a multi-socket connector.

13. The headband assembly of claim 1, wherein said power management network has a second power output connecter, and supplies power from said battery port to said second power output connector.

* * * * *